United States Patent [19]

Williams

[11] Patent Number: Plant 6,821

[45] Date of Patent: May 30, 1989

[54] LITTLE STARBURST ROSE PLANT

[75] Inventor: J. Benjamin Williams, Silver Springs, Md.

[73] Assignee: NPI, Salt Lake City, Utah

[21] Appl. No.: 153,703

[22] Filed: Feb. 8, 1988

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

A new and distinct variety of rose plant of the miniature rose class, which was originated by my crossing an unnamed seedling of Prominent as seed parent and Rise 'n Shine as pollen parent; characterized by striking deep yellow flowers highlighted by a deep orange-red wash at the tip and point of recurl, resulting in a fiery effect. The exceptionally fragrant flowers are borne singly on long, strong cutting canes on this upright, spreading, and vigorous growing plant.

1 Drawing Sheet

1

The present invention relates to a new and distinct variety of rose plant of the miniature rose class named "Little Starburst," which was originated by my crossing as seed parent as unnamed seedling of "Prominent" (U.S. Plant Pat. No. 3,380) and the rose known as "Rise 'n Shine" (U.S. Plant Pat. No. 4,231) as pollen parent.

Among the novel characteristics possessed by this new variety which distinguishes it from all other varieties of which I am aware are:

1. High-centered flowers of deep yellow blending to a deep orange-red washing at edge of petals, particularly at tip and point of recurl.
2. The elegantly tapered buds open slowly to flowers approximately 1¾ to 2" with thick deep yellow petals brushed by a burnished orange-red at edge of petals, giving a flame-like effect when fully opened.
3. This medium-sized plant produces its long-holding flowers singly on long cutting canes, followed by two or three close secondary blooms arising from the next leaf axil.
4. This sturdy plant is vigorous and branching, with a spreading characteristic, growing 12–18" in height, and is covered with good-sized medium green foliage.
5. The striking blooms of this rose are especially fragrant.

Asexual reproduction by budding of the new variety as performed in Silver Spring, Md., and West Grove, Pa., shows that the foregoing and other distinguishing characteristics come true to form and are established and transmitted through succeeding propagation.

The new and improved rose variety which I have developed is a striking new miniature with blooms of deep yellow at the base, blending to a lighter yellow and washed with a bright orange-red at the edge of the petals. The petals have a uniquely thick texture which enhances holding quality and extends bloom life. The particularly fragrant flowers are borne singly on strong, long cutting canes, with two or three secondary blooms following. The foliage on this vigorous and spreading plant is good-sized and medium green. Its good holding quality makes it ideally suitable for arrangements, as well as for use in the garden.

The accompanying drawing shows typical specimens of the vegetative growth and flowers of the new variety in different stages of development and as depicted in color as nearly true as it is reasonably possible to make the same in a color illustration of this character.

2

The following is a detailed description of my new variety, with color terminology in accordance with the Royal Horticultural Society Colour Chart (RHSCC). The terminology used in color description herein refers to plate numbers in the aforementioned color chart, e.g., "10A" is plate 10-A of The Royal Horticultural Society Colour Chart.

Parentage: Seedling.

*Seed parent.*—An unnamed seedling of "Prominent".

*Pollen parent.*—"Rise 'n Shine".

Class: Miniature.

The following observations are made of specimens grown outdoors at Silver Spring, Md., and West Grove, Pa., during the months of June through September.

FLOWER

Blooming habit: Continuous.

A. Bud:

(1) *Size.*—Medium.
(2) *Form.*—Tapered.
(3) *Color.*—When sepals first divide: near 10-C blending near 46-A at tip. When petals begin to unfurl, near 10-A blending to 42-A at tip and point of recurl.
(4) *Sepals.*—Extends slightly beyond bud.
(5) *Peduncle.*—Length 5½ cm. Aspect — straight. Strength — heavy. Color — 144-A.

B. Bloom:

(1) *Size.*—1¾ to 2".
(2) *Borne.*—Individually on long cutting canes.
(3) *Form.*—High-centered, with petals recurling; petals quilled on open flower.
(4) *Petalage.*—24–26.
(5) *Color.*—During first two days. Center of flower — near 45-A. Outer petals near 34-A. Base of petals: near 10-A. Reverse of petals — near 10-D blending to 34-A.
(6) *Color change.*—General tonality from a distance is a deep golden yellow highlighted by a fiery red-orange wash at the edge of the petals. Color is well maintained.

C. Petals:

(1) *Texture.*—Thick.

(2) *Appearance.*—Velvety.
(3) *Form.*—Diamond shaped and strongly recurled.
(4) *Arrangement.*—Regularly arranged shingly-like overlay.
(5) *Petaloids in center.*—Few.
(6) *Persistence.*—Drops off cleanly.
(7) *Fragrance.*—Exceptionally fragrant.
(8) *Lasting quality.*—5–9 days on plant, 3–5 days as cut flower.

REPRODUCTIVE ORGANS

A. Stamens, anthers: Irregularly arranged around styles.
(1) *Color.*—Yellow-orange, near to 14-B.
B. Pollen: Color is golden yellow, near to 14-B.
C. Styles: Thin, medium length.
D. Stigmans:
*Color.*—Orange-red — 33-A.
E. Hips: Green and globular, ripening to bright orange.

PLANT

A. Form: Upright and spreading.
B. Growth: Very Vigorous.
*Height attained.*—12–16 in.
C. Foliage: Compound of 5 to 7 leaflets.
(1) *Size.*—Large.
(2) *Quantity.*—Abundant.
(3) *Color.*—New foliage: upper side — 137-B, under side — 147-C. Old foliage: upper side — 137-CB, under side — 147-D.
(4) *Shape.*—Oval, pointed.
(5) *Texture.*—Upper side — somewhat shiny, smooth. Under side — rough and dull.
(6) *Edge.*—Serrated.

(7) *Serration.*—6 per cm.
(8) *Leaf stem.*—Color — 138-A; under side — 138-B.
(9) *Stipules.*—Medium.
D. Wood:
(1) *New wood.*—Color — 146-A. Bark — smooth.
(2) *Old wood.*—Color — 146-A. Bark — smooth.
E. Thorns:
(1) *Thorns.*—Quantity: on main stalks from base — ordinary; on laterals from stalk — very few. Form: flat base, pointed slightly downward. Length: long. Color when young — 22-A. Position: irregular.
(2) Prickles.—Quantity: On main stalks — few; on laterals — none.
F. Plant's disease resistsance:
(1) *Mildew.*—Excellent.
(2) *Blackspot.*—Excellent.
(3) *Rust.*—None observed.
G. Winter hardiness: Completely winter hardy.

I claim:

1. A new and distinct variety of rose plant of the miniature rose class, substantially as shown and described, characterized particularly as to novelty by elegantly tapered buds opening to high-centered deep yellow flowers bleeding to a bright orange-red at the tip and point of recurl; its large, medium-green foliage; its exceptional fragrance; its habit of producing blooms singly on long, strong cutting canes; its vigorous habit of growth and hardiness; and particularly good holding quality resulting from the unique, heavy texture of the petals.

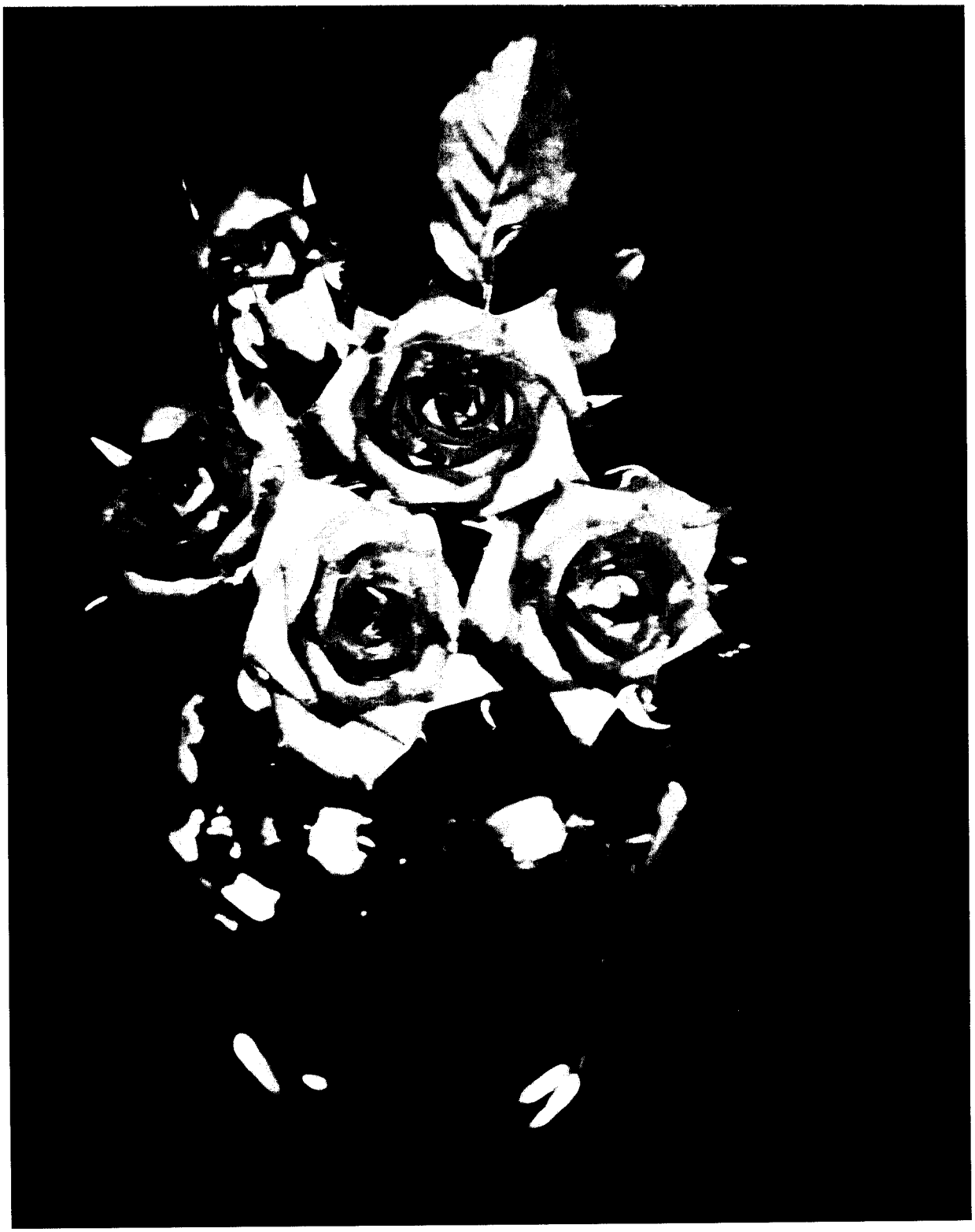

* * * * *